(12) United States Patent
Seino et al.

(10) Patent No.: US 7,400,753 B2
(45) Date of Patent: Jul. 15, 2008

(54) BIOLOGICAL SAMPLE OPTICAL MEASURING METHOD AND BIOLOGICAL SAMPLE OPTICAL MEASURING APPARATUS

(75) Inventors: Taisaku Seino, Hitachinaka (JP);
Satoshi Takahashi, Hitachinaka (JP);
Kenji Yasuda, Tokyo (JP); Yoshitada Oshida, Chigasaki (JP)

(73) Assignee: Hitachi, Ltd., Tokyo (JP)

( * ) Notice: Subject to any disclaimer, the term of this patent is extended or adjusted under 35 U.S.C. 154(b) by 907 days.

(21) Appl. No.: 10/482,614

(22) PCT Filed: Jul. 3, 2001

(86) PCT No.: PCT/JP01/05752

§ 371 (c)(1),
(2), (4) Date: Jul. 16, 2004

(87) PCT Pub. No.: WO03/005005

PCT Pub. Date: Jan. 16, 2003

(65) Prior Publication Data

US 2004/0239916 A1    Dec. 2, 2004

(51) Int. Cl.
*G06K 9/00* (2006.01)

(52) U.S. Cl. .................. 382/128; 382/130; 382/131; 382/132; 382/284; 382/294

(58) Field of Classification Search .............. 382/128, 382/130, 131, 132, 284, 294
See application file for complete search history.

(56) References Cited

U.S. PATENT DOCUMENTS

| 6,420,183 B1 * | 7/2002 | Krahn et al. ........... 436/164 |
| 6,614,452 B1 * | 9/2003 | Cable ..................... 715/764 |
| 7,010,149 B1 * | 3/2006 | Knoplioch et al. ...... 382/128 |

FOREIGN PATENT DOCUMENTS

| JP | 6-308118 | 11/1994 |
| JP | 6-331441 | 12/1994 |
| JP | 8-271410 | 10/1996 |
| JP | 8-334466 | 12/1996 |
| JP | 10-185803 | 7/1998 |

\* cited by examiner

*Primary Examiner*—Bhavesh Mehta
*Assistant Examiner*—John B Strege
(74) *Attorney, Agent, or Firm*—Dickstein Shapiro LLP

(57) ABSTRACT

A fluorescent or luminescence image of at least part of a biological sample is imaged, then a transmission light image of at least part of the biological sample is imaged, and thereafter the fluorescent or luminescence image and the transmission light image are overlaid such that the identical area of the sample is coincided to display. The present invention allows detecting the accurate location of fluorescence or luminescence in a given part of the biological sample.

14 Claims, 7 Drawing Sheets

FLUORESCENT IMAGE
(RESOLUTION OF 2 μm)

TRANSMISSION IMAGE
(RESOLUTION OF 1 μm)

UNINFECTED
(NEGATIVE)

UNINFECTED (NEGATIVE)   PLASMA INFECTION (POSITIVE)   NUCLEAR INFECTION (POSITIVE)

BIOLOGICAL SAMPLE OPTICAL MEASURING METHOD AND BIOLOGICAL SAMPLE OPTICAL MEASURING APPARATUS

TECHNICAL FIELD

The present invention relates to a method and an apparatus for optical analysis of biological samples, by imaging fluorescent images and transmitted images of biological samples.

BACKGROUND

There are methods for common cytodiagnosis and epidemic analysis by detecting epidemia or anomaly by reacting pathogenic viruses or tumor cells with fluorescence labeled antibody or nucleic acid probe (Journal of Medical Technology, extra issue, "cytology—view to the 21st century" vol. 44, no. 11, October 2000, Igaku-shoin pub., Tokyo). Since fluorescent-labeled substances may non-specifically be absorbed to any matter or wall surfaces other than the target, it may be desirable that the fluorescent label should be compared with an image depicting the actual structure of cell or tissue, in order to detect the presence of a viral strain in question or a gene in the cell or tissue. The imaging of both fluorescent image and the actual image may be performed in general by means of conventional fluorescence microscopy, in condition that a specimen dedicated for the fluorescent imaging is prepared separately along with another specimen used for the actual image (stained image). The difference between smear sample may be negligible for two adjoining thin sections of cells; however, smear sample which may be unique and difficult to prepare another same reproduction, may prevent from conducting an accurate determination based upon different smear sample.

When attempting from one specimen to obtain the fluorescent-labeled image and stained image at the same time, the pigment (dye) used for the staining may interfere the fluorescent measurement, thus it may be wise to devise a method so as to avoid such interference. Although for example, it can be possible to obtain a transmitted image without staining by using the phase difference, a contrast as sharp as the stained image is unlikely obtainable. Also a highly coincided registration of optical cell image with fluorescent image is almost impossible to obtain with a manually operated microscope.

There is disclosed a Japanese Unexamined Patent Publication No. 2000-310637 for a method of cytological measurement. In the above document by labeling with luminescence chemical, the stained cytological structure is observed after targeting the microscopic field to the luminescence location detected by the light-emitting image. This method evaluates the luminescence image and stained image separately, so that the discrimination of relationship between the luminescence label and actual cell is extremely difficult as above.

In addition, Japanese Unexamined Patent Publication No. Hei8-112099 document discloses a method of imaging fine picture of body specimen by a tunnel SEM (Scanning Electron Microscope) while capturing the fluorescent light emitted by such radiation as of fine electron beam with a photo-electronic converter to superpose on the fine image another image data obtained by the photo-electronic converter. This method however may have a problem that the apparatus for obtaining final images becomes very complicated because of detection of fluorescent light at the same time as capturing a fine image by tunnel SEM.

Therefore in the conventional methods of clinical analysis as above may involve operation of microscope and staining, resulting in inadvertent errors caused by the physical fatigue of operators.

SUMMARY

The present invention has been made in view of the above circumstances and has an object to overcome the above problems and to provide a method and apparatus for optical measurement of biological samples, which allow detecting much accurate location of fluorescence or luminescence from a given location on a biological sample.

The present invention having achieved the above objects may incorporate:

(1) A method of optical measurement of biological samples, comprising the steps of:
  imaging fluorescent or luminescence image of at least a part of a biological sample;
  imaging a transmission image of at least a part of said biological sample; and
  displaying said fluorescent or luminescence image and said transmission light image superimposingly, such that said fluorescent or luminescence image of said biological sample correspond to said transmission light image of said biological sample.

(2) A method of optical measurement of biological samples of (1), wherein:
  said transmission light image has much higher resolution in comparison with said fluorescent or luminescence image.

(3) A method of optical measurement of biological samples of (1), wherein:
  the resolution of said transmission light image is in the range of from twice to twenty times of the resolution of said fluorescent or luminescence image.

(4) A method of optical measurement of biological samples of (1), wherein:
  after having captured said fluorescent or luminescence image said biological sample is stained and then said transmission light image is imaged.

(5) A method of optical measurement of biological samples of (1), wherein:
  with reference to an optical identification mark provided on a retainer for retaining said biological sample for registration, said fluorescent or luminescence image and said transmission light image are registered for imaging.

(6) An apparatus of optical measurement of biological samples, which comprises:
  image data storage capability for storing fluorescent or luminescence image having at least a part of a biological sample measured and transmission light image having at least a part of said biological sample measured; and
  computing capability for computing on said fluorescent or luminescence image and said transmission light image;
  wherein:
  said fluorescent or luminescence image and said transmission light image stored in said image data storage capability are processed by said computing capability to then display said fluorescent or luminescence image and said transmission light image superimposingly.

(7) An apparatus of optical measurement of biological samples of (6), which further comprises:
  an optical measurement means for measuring said fluorescent or luminescence image and said transmission light image.

(8) An apparatus of optical measurement of biological samples of (7), wherein:
said optical measurement means images said fluorescent or luminescence image at a higher resolution than said transmission light image.

(9) An apparatus of optical measurement of biological samples of (6), which further comprises:
a holder for holding said biological sample having optical identification marks;
wherein:
said fluorescent or luminescence image is imaged registered with said transmission light image.

(10) An apparatus of optical measurement of biological samples set forth in (9), in which:
said optical identification mark is a plurality of circle patterns; and
the registration for imaging of said fluorescent or luminescence images and transmission light image is performed by referencing a center point coordinate of said circle pattern obtained from the image data of said optical identification mark.

(11) An apparatus of optical measurement of biological samples of (7) wherein:
said optical measurement means images said fluorescent or luminescence images, then the transmission light image after having stained said biological sample for transmission light image measurement.

(12) An apparatus of optical measurement of biological samples of (6) which further comprises:
a staining means for staining said biological sample.

(13) An apparatus of optical measurement of biological samples of (6) wherein:
a fluorescent or luminescence image is obtained from the biological sample having fluorescent or luminescence substance conjugated, thereafter a transmission light image is obtained from said biological sample having stained.

(14) An apparatus of optical measurement of biological samples, which comprises:
a fluorescence or luminescence detecting unit for detecting fluorescence or luminescence emerged from a biological sample;
a transmission detecting unit for emitting light to said biological sample and for detecting the transmission light of the emitted light having passed through said biological sample;
an image storage unit for storing image data of fluorescent or luminescence images measured by said fluorescence or luminescence detecting unit and transmission light images measured by said transmission detecting unit;
image data processing unit for processing image data of said fluorescent or luminescence images and image data of said transmission light images stored on said image data storage unit; and
image display unit for displaying said fluorescent or luminescence image superposed on said transmission light image after having processed on said image data processing unit said image data of said fluorescent or luminescence image and said image data of said transmission light image.

(15) An apparatus of optical measurement of biological samples of (14), wherein:
said fluorescence or luminescence detecting unit emits an optical beam to scan said biological sample in order to detect fluorescence excited by the emitted optical beam from said biological sample.

(16) An apparatus of optical measurement of biological samples of (14), wherein:
said fluorescence or luminescence detecting unit detects light luminescence caused by the luminescence treatment processed to said biological sample.

(17) An apparatus of optical measurement of biological samples of (14), wherein:
said fluorescence or luminescence detecting unit has fluorescence excited from said biological sample input for two dimensional image information, said transmission detector unit has transmission light image information of higher resolution than the two dimensional image information input to said fluorescence or luminescence detector unit.

DESCRIPTION OF SYMBOLS

1—biological sample, 1-1a, b,c—identification mark, 2—biological sample holder unit, 3—biological sample holder driving unit, 3-1—supporting guide, 3-2—θ axis adjusting stage, 3-3—X axis direction fine adjuster stage, 3-4—Y axis direction fine adjustment stage, 3-5—X axis direction coarse adjustment stage, 3-6—controller unit, 4—laser light source, 5—excitation light optics, 6—long-pass filter, 7—fluorescence optics, 8—fluorescence detection unit, 9—transmission light source, 10—transmission light optics, 11—two dimensional color image sensor, 12—fluorescent image storage unit, 13—transmission light image storage unit, 14—image buffer, 15—image data processor unit, 16—image display unit, 17—mercury-vapor lamp, 18—bandpass filter, 19—two dimensional monochrome image sensor, 20—biological sample holder unit, 21—sample staining unit, 22—staining solution sprayer unit, 23—solution collecting unit, 24—rinse solution sprayer unit, 25—rinse collecting unit, 26—group of stain solution containers, 26-1—stain A container, 26-2—stain B container, 26-3—clearing solution container, 26-4—tubing cleaning solution container, 27—rinse solution containers, 27-1—rinse solution container, 27-2—fractioning solution container, 27-3—affinity solution A container, 27-4—affinity solution B container, 28—electromagnetic valves, 29—electromagnetic valves, 30—electromagnetic valves, 31—electromagnetic valves, 32—stain solution feeder pump, 33—stain solution collecting pump, 34—rinse solution feeder pump, 35—rinse solution collection pump, 36—stain solution tubings, 37—rinse solution tubings, 38—waste rinse solution container,

DETAILED DESCRIPTION

A detailed description of one preferred embodiment embodying the present invention will now be given. However a scope of the present invention is not be limited the following embodiment.

Figure 1:
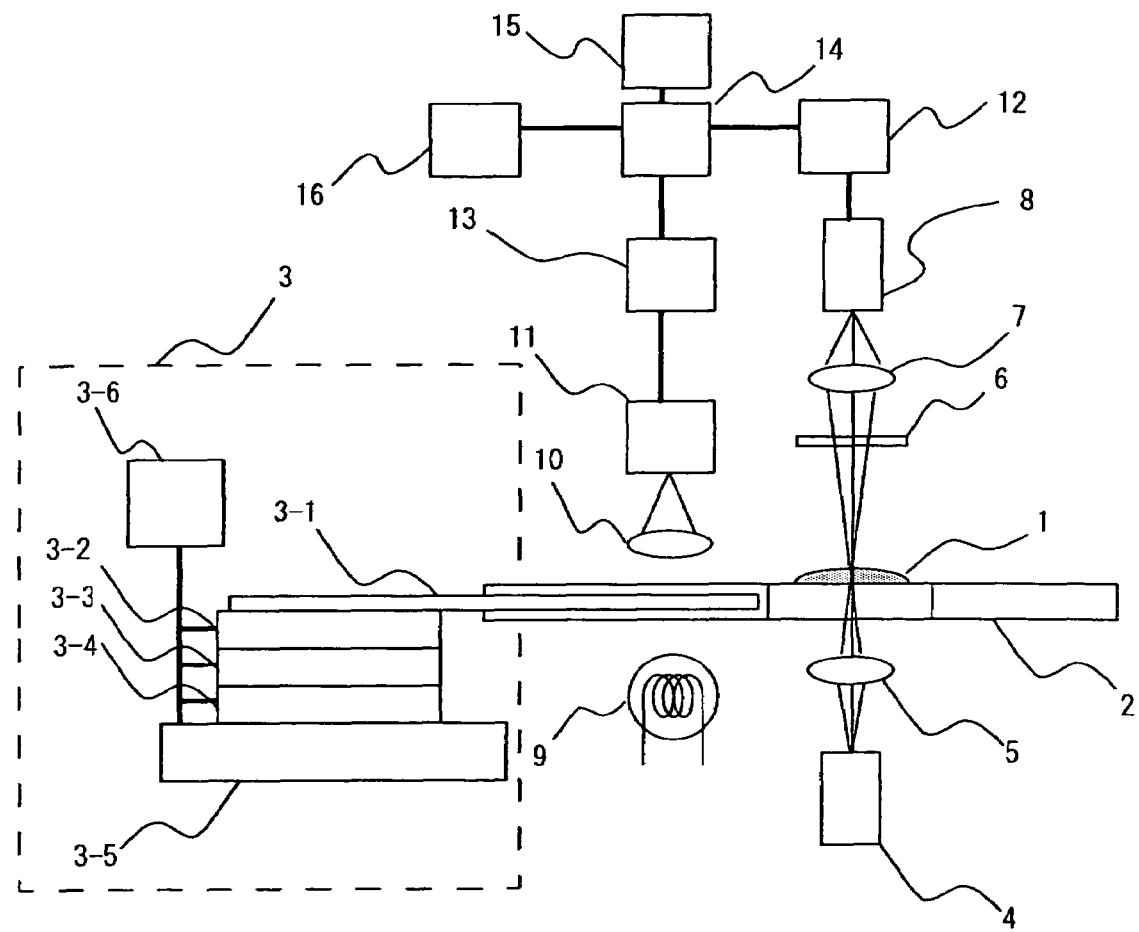
FIG. 1 is a schematic diagram of substantial part of a biological sample optical measurement apparatus incorporating the present invention.

FIG. 1 shows a biological sample optical measurement apparatus incorporating the present invention. The optical measurement apparatus includes a biological sample holder unit 2 carrying a biological sample 1, and a biological sample holder driving unit 3 for driving the biological sample holder unit 2 to a desired position. The optical measurement apparatus may analyses the biological sample 1 to determine whether there is an infection of a viral strain such as HPV, HCV, or HIV, and may identify the infected location of viruses. The sample 1 may include for example an anatomy section, cultured cell, or smear preparation to be examined, and in this context the sample is assumed to be hybridized with a probe DNA. The probe DNA includes a sequence that can be hybridized to a DNA derived from the viral strain to examine, and is bound to fluorescent label. Any fluorescent label can be used which may, in response to the excitation laser luminescence of a predetermined wavelength, emit fluorescence of the wavelength longer than the excitation laser, but may not be limited thereto. More specifically, the exemplary fluorescent labels may include Cy-2, Cy-3, Cy-5, and Cy-7, fluorescent substance available from the Amersham Pharmacia Biotech, Corp. Instead of binding a fluorescent label, a chemical or biological luminescence substance can be bound to the probe DNA. Some examples of usable chemical or biological luminescent substance may include alkaline phosphatase, luciferase, luciferin, peroxidase, and luminol.

Biological sample holder driving unit 3 comprises a supporting guide 3-1 for supporting the biological sample holder unit 2, a θ axis adjusting stage 3-2 for revolving the biological sample holder unit 2 to its in-plane direction (θ axis), an X axis direction fine adjuster stage 3-3 for moving the biological sample holder unit 2 in a predetermined in-plane direction (X axis), a Y axis direction fine adjustment stage 3-4 for moving the biological sample holder unit 2 in another predetermined in-plane direction perpendicular to the X axis (Y axis), and an X axis direction coarse adjustment stage 3-5 for relatively largely moving the biological sample holder unit 2 in the X axis direction. The biological sample holder driving unit 3 also is equipped with a driver controller unit 3-6 for controlling the operation of the θ axis adjusting stage 3-2, X axis direction fine adjuster stage 3-3, Y axis direction fine adjustment stage 3-4, and X axis direction coarse adjustment stage 3-5. The operation control of the X axis direction fine adjuster stage 3-3 and the Y axis direction fine adjustment stage 3-4 by the controller unit 3-6 allows scanning the biological sample holder unit 2 carrying the biological sample 1 in the desired direction.

The optical measurement apparatus further comprises a laser light source 4 for luminescence excitation for measuring the fluorescent image of the biological sample 1 carried on the biological sample holder unit 2, an excitation light optics 5, a long-pass filter 6, a fluorescence optics 7, and a fluorescence detection unit 8. The laser light source 4 for exciting fluorescence may consist, for example, a semiconductor laser device, YAG laser device, He—Ne laser device, or Ar laser device and the like, capable of emitting excitation laser of a predetermined wavelength. A suitable laser light source 4 for exciting fluorescence, which may emit an excitation laser of the desired wavelength, may be selected in accordance with the type of luminescence label substance bound to the probe DNA. For example, when using a plurality of numbers of luminescence label substances, a laser light sources 4 suitable for emitting the laser of a plurality of wavelength each corresponding to a respective fluorescence label, or a plurality of laser light sources 4 each suitable for emitting the laser of a wavelength corresponding to a respective fluorescence label may be used for the laser light source 4. The excitation light optics 5 may include lenses and the like and may be capable to focus the exciter laser beam emitted from the laser light source 4 for excitation of fluorescence onto the biological sample 1. The long-pass filter 6 may transmit component of the beam of the wavelength longer than a predetermined wavelength. The fluorescence optics 7 may include a convergence lens, and serves as a convergence optics for the luminescence passed through the long-pass filter 6. The fluorescence detection unit 8 may include a photosensor for example an electron intensifier or a CCD, for detecting the fluorescence collected by the fluorescence optics 7 and for convert the fluorescent intensity of the detected luminescence to digital data.

The optical measurement apparatus may further comprises, for measuring the transmission light image of the biological sample 1 carried on the biological sample holder unit 2, a transmission light source 9, a transmission light optics 10, a two dimensional color image sensor 11. The transmission light source 9 may be for example a halogen lamp, which may emit the transmission light to transmit through the biological sample 1. The transmission light optics 10 may include some lenses and the like to collect the transmission light having transmitted through the biological sample 1. The two dimensional color image sensor 11 may detect the transmission light collected by the transmission light optics 10 to convert the color image of thus detected transmission light into the image data of R, G, B colors.

The optical measurement apparatus may further comprise a fluorescent image storage unit 12 for storing digital data on the fluorescent image obtained by the fluorescence detection unit 8, a transmission light image storage unit 13 for storing the image data obtained by the two dimensional color image sensor 11, an image buffer 14 for reading out and save the digital data and image data stored in the fluorescent image storage unit 12 and the transmission light image storage unit 13 respectively, an image data processor unit 15 for processing the digital data and image data stored on the image buffer 14 to generate a display image data, an image display unit 16 for displaying a merged image of the fluorescent image and transmission light image from the display image data generated by the image data processor unit 15 and stored in the image buffer.

Figure 2:
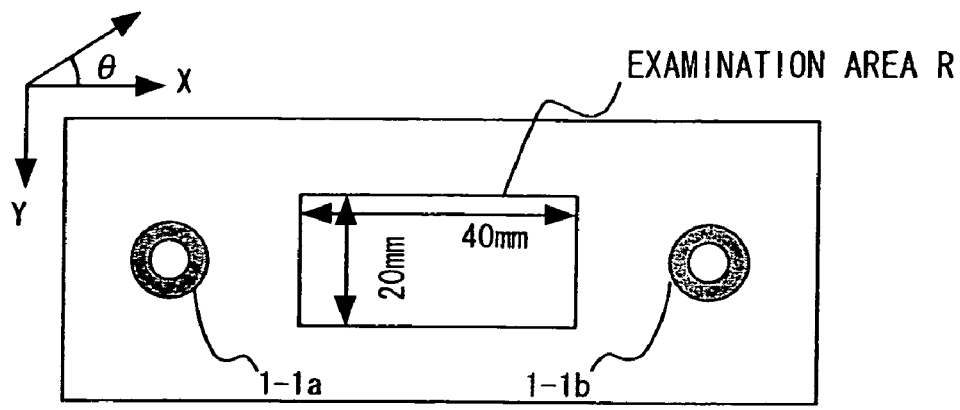
FIG. 2a is a schematic top plain view of substantial part of a biological sample holder.
FIG. 2b is a schematic top plain view of substantial part of another biological sample holder.
FIG. 2c is a schematic top plain view of substantial part of still another biological sample holder.
Figure 2:
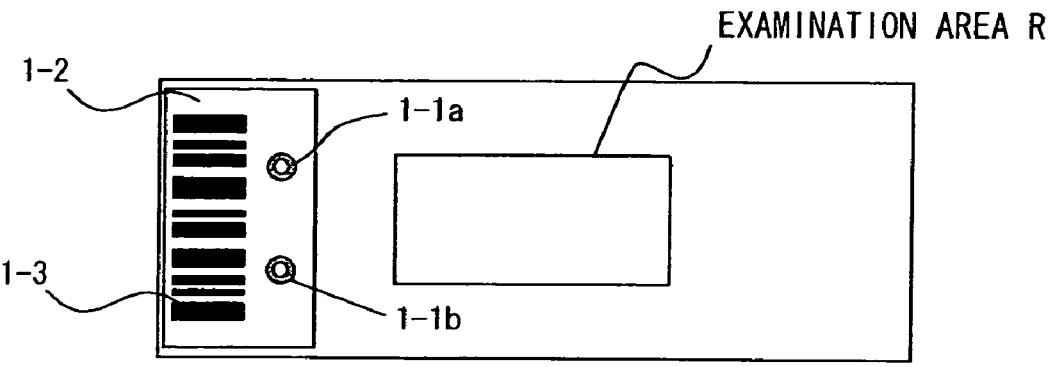
Figure 2:
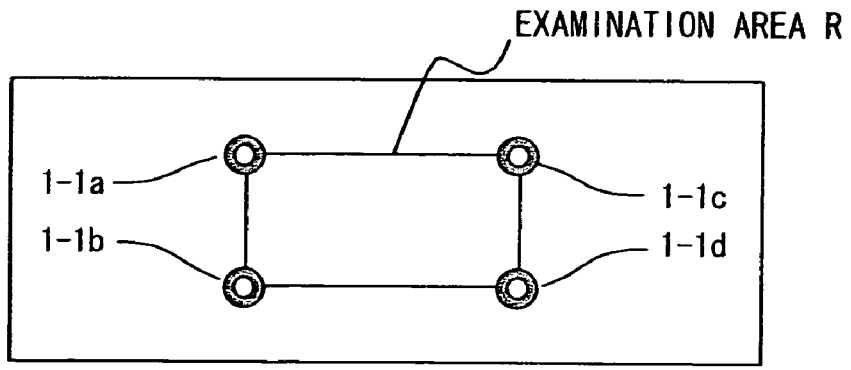

The biological sample holder unit 2 on the other hand may have an examination area R and an identification mark for accurate registration in the optical measurement apparatus, as shown in FIGS. 2a to 2c. It is to be note here that FIGS. 2a to 2c illustrate some variations of the biological sample holder unit 2.

The biological sample holder unit 2 shown in FIG. 2a comprises a substrate, an examination area R located at about the center of the substrate, a pair of identification marks 1-1a and 1-1b placed on the both sides of the examination area R. The substrate may be a quartz glass of the thickness of 0.5 to 1.5 mm, or a material that the examination area R is transparent to the excitation laser described above. Each of identification marks 1-1a and 1-1b is composed of concentric circles of the diameter of approximately 5 to 100 μm, and may be formed by etching the substrate to form the ring shape and by printing the fluorescent agent within the circles. Thus formed identification marks 1-1a and 1-1b may be identified by both of the fluorescence detection unit 8 and the two-dimensional color image sensor 11.

The biological sample holder unit 2 shown in FIG. 2b includes a bar-code 1-3 recorded the information on the sample on the commercially available slide glasses, and the identification marks 1-1a and 1-1b are formed on a tag sticker 1-2 having the bar-code 1-3 printed thereon. In other words, the biological sample holder unit 2 shown in FIG. 2b may be constituted by patching a tag sticker 1-2 on anywhere other than the examination area R of the commercially available stage glasses.

Moreover, the biological sample holder unit 2 shown in FIG. 2c comprises a substrate, an examination area R located at about the center of the substrate, four identification marks 1-1a, 1-1b, 1-1c and 1-1d placed on the four corners of the examination area R. In other words, the biological sample holder unit 2 shown in FIG. 2c has a rejoin surrounded by those four identification marks 1-1a, 1-1b, 1-1c, and 1-1d in this order as the examination area R.

Figure 3:
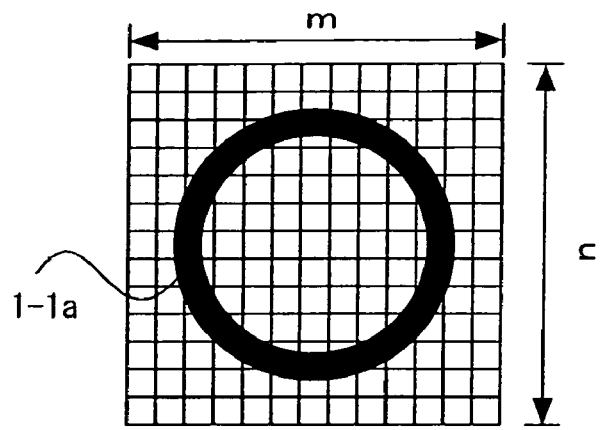
FIG. 3a is a schematic diagram illustrating the registration in accordance with the present invention, indicating the transmission light image of identification marks.
FIG. 3b is a schematic diagram illustrating the registration in accordance with the present invention; indicating a digitized transmission light image.
FIG. 3c is a schematic diagram illustrating the registration in accordance with the present invention; indicating the characteristics of intensity distribution of "row" side.
FIG. 3d is a schematic diagram illustrating the registration in accordance with the present invention; indicating the characteristics of intensity distribution of "column" side.
Figure 3:
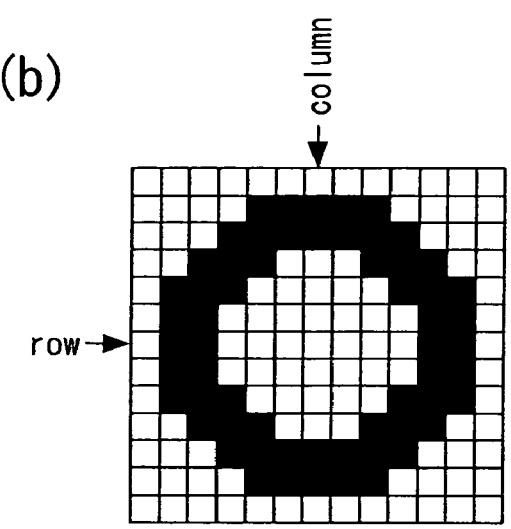
Figure 3:
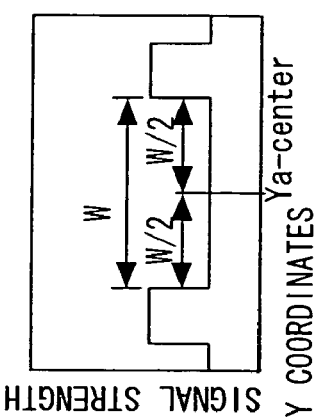
Figure 3:
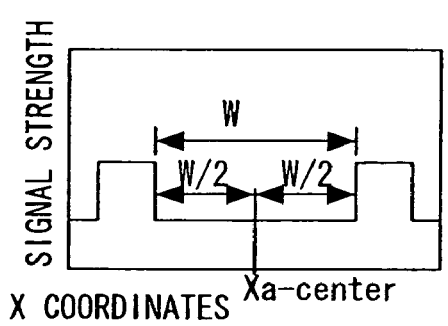

The registration of the biological sample holder unit 2 shown in FIGS. 2a to 2c may be performed by referring to the identification marks 1-1a, 1-1b (and 1-1c, 1-1d) as follows. At first, moving the identification mark 1-1a so as to be within the examination area of the transmission light image to measure the transmission light image of the identification mark 1-1a (FIG. 3a). Then, the distance is determined between the origin of the X axis direction fine adjuster stage 3-3 and the Y axis direction fine adjustment stage 3-4 obtained from the controller unit 3-6 and the center position of the identification mark 1-1a.

More specifically, thus obtained transmission light image of the identification mark 1-1a is digitized to obtain a digital image of the identification mark 1-1a (FIG. 3b) of a matrix of m by n pixels. Then the intensity distribution on the "row" side is determined (FIG. 3c). More specifically, in a graph indicating the relationship between the signal strength and the X coordinates as shown in FIG. 3c, W is set so as for the interval between the maximum values of signal strength to be maximum, so that the X coordinate at W/2 is determined to be the center in the X axis direction of the identification mark 1-1a (Xa-center). In a similar manner, the intensity distribution of the "column" side of thus obtained digital image is determined (FIG. 3d), to determine the center of the identification mark 1-1a in the Y-axis direction (Ya-center). In this manner, the center point of the identification mark 1-1a can be given as a coordinate (Xa-center, Ya-center). The center coordinate (Xa-center, Ya-center) of thus given identification mark 1-1a is set to be the origin of image measurement as will be described later. The center coordinate of the identification mark 1-1a is recorded in the controller unit 3-6.

Next, the X axis direction fine adjuster stage 3-3 and the Y axis direction fine adjustment stage 3-4 are driven to measure the transmission light image of the identification mark 1-1b to determine the center coordinate of the identification mark 1-1b. The center coordinate of the identification mark 1-1b can be determined as (Xb-center, Yb-center), as similar to the coordinate of identification mark 1-1a.

Then, the θ axis adjusting stage 3-2 is driven to collimate the X axis with the linear segment connecting the center points of the identification marks 1-1a and 1-1b. In other words, the θ axis adjusting stage 3-2 is driven such that the angle formed by the line connecting the center points of the identification marks 1-1a and 1-1b with the X axis becomes 0. More specifically, the θ axis adjusting stage 3-2 is driven so as for the Ya-center and Yb-center of the center coordinate of identification mark 1-1a (Xa-center, Ya-center) to be consistent with the center coordinate of identification mark 1-1b (Xb-center, Yb-center).

Then, the origin of the biological sample holder unit 2 is set to be on the center coordinate of the identification mark 1-1a for imaging the transmission light image and fluorescent image. The origin used for imaging the transmission light image and fluorescent image can be obtained as have been described above. The biological sample holder unit 2 shown in FIG. 2a is capable of confirming the position of the identification marks 1-1a and 1-1b at the time of registration at a higher precision and in a shorter time. The biological sample holder unit 2 shown in FIG. 2b can use the commercially available slide glasses as expendables, allowing decreasing the cost. The biological sample holder unit 2 shown in FIG. 2b can store in a bar-code the sample information encoded in a bar-code, when removed from the optical measurement apparatus, facilitating the management of samples 1. By recording the image data of captured transmission light image and/or fluorescent image in relation thereto, the management of the biological sample holder unit 2 may be facilitated as well as the management of samples 1. The biological sample holder unit 2 shown in FIG. 2c has identification marks 1-1a, 1-1b, 1-1c, 1-1d on the four corners of the examination area R, the examination area R can be recognized at a higher resolution in a shorter time simultaneously with the registration described above. The examination area R can be recognized easily if the biological sample holder unit 2 is in a different form.

It should be appreciated that the biological sample holder unit may not be limited to those shown in FIGS. 2a to 2c, but may be one which registers using an edge of the biological sample holder unit 2 as the referential end, or which marks any given location in the vicinity of the examination area R by means of a fluorescent bead and the like at the time of mounting the sample 1 for use as the origin. In such cases no special procedure is required for the biological sample holder unit 2 to achieve the registration for the image measurement.

As can be appreciated from the foregoing description, by using the optical measurement apparatus having biological sample holder unit 2 registered the fluorescent image and transmission light image of the sample 1 is imaged in a manner as will be described below. In this embodiment, A DNA probe having a base sequence hybridized with the DNA derived of a viral strain is bound to a fluorescent label, Cy-5 (R) available from Amersham Pharmacia Biotech, Corp., thus bound DNA probe is used to identify and determine the infection by the virus and infected lesion with respect to the examining cell.

On the optical measurement apparatus, the fluorescent image of the sample 1 is imaged. At the time of imaging the fluorescent image, the exciting laser from the laser light source 4 is emitted to the biological sample 1. Since Cy-5(R) fluorescent label available from Amersham Pharmacia Biotech, Corp. is used in this embodiment, a semiconductor laser, which may emit the exiting laser of the wavelength of 635 nm, is used for the laser light source 4. When emitting the exciting laser, fluorescence of the wavelength of 670 nm or longer can be observed in the target cell. The fluorescence observed in the cell may pass through the long-pass filter 6, may be collected by the fluorescence optics 7, and may be incident into the fluorescence detection unit 8. The fluorescent exciting laser is blocked by the long-pass filter 6 to prevent the laser from being incident into the fluorescence detection unit 8.

The detection of fluorescence of the biological sample 1 is achieved thereby. The fluorescent intensity thus detected may be converted for example into digital data of 16-bit width to store in the fluorescent image storage unit 12. At this time the exciting laser can be converged by the excitation light optics 5 to focus on a spot of the diameter equal to or less than 10 μm. Then the exciting laser beam is emitted to the biological sample 1 from the backside of the biological sample holder unit 2 while the biological sample holder driving unit 3 moves the biological sample holder unit 2 to scan by the moving spot irradiated by the exciting laser to detect the fluorescence by the fluorescence detection unit 8. The fluorescence detection unit 8 thereby may obtain the fluorescent image of the resolution of 10 μm.

At this point, as the sample 1 is hybridized by the probe DNA corresponding to the viral strain to be examined, primary screening whether the infection by the target virus exists can be achieved by examining the presence or absence of the fluorescence from the sample 1. When there is observed fluorescence from the biological sample 1 during the primary screening, the location of fluorescence is recorded by the controller unit 3-6 to use as the reference measurement position at the time of registration for the transmission light image measurement as described later. In this embodiment, since the fluorescent excitation is laser-induced by the exciting laser converged equal to or smaller than the diameter of 10 μm, the radiation intensity with respect to the fluorescent label may be increased, and as a result the amount of fluorescence emitted from the fluorescent label may be increased, in order to improve the detection sensitivity of the fluorescence.

When using one fluorescent label different for each of a plurality of probe DNAs, a laser light source 4 capable of emitting exciting laser of different wavelengths should be used. This allows detecting a plurality of wavelengths of fluorescence observed in the sample 1, to thereby obtain the fluorescent images for those plural wavelengths of fluorescence.

Next, for those samples 1 having the presence of fluorescent label confirmed on the fluorescent image, the transmission light image is examined. Prior to the measurement of transmission light image, it is preferable that the sample 1 having fluorescent image measured is removed from the optical measurement apparatus along with the biological sample holder unit 2 to stain the biological sample 1 so as to be able to observe the cell structure contained in the sample 1. After staining, the biological sample holder unit 2 is reattached to the biological sample holder driving unit 3.

At this time by observing the identification marks 1-1*a* and 1-1*b* of the biological sample holder unit 2, with the two dimensional color image sensor 11, in a manner similar to the registration of the biological sample holder unit 2 as have been described above with reference to FIG. 3, the θ axis adjusting stage 3-2 is driven until the angle θ of the linear segment connecting the center point of the identification mark 1-1*a* with the center point of the identification mark 1-1*b* with the x-axis becomes 0 for the compensation for the alignment, while at the same time the center coordination of the identification mark 1-1*a*, namely the origin is matched. More specifically, the X axis direction fine adjuster stage 3-3 and the Y axis direction fine adjustment stage 3-4 is driven such that the center of the identification mark 1-1*a* observed through the two dimensional image sensor 11 is coincided with the center coordinate of the identification mark 1-1*a* stored in the controller unit 3-6.

Next, the transmission light image of the sample 1 is imaged. For the imaging of the transmission light image, the X axis direction coarse adjustment stage 3-5 is driven to move the biological sample holder unit 2 until the location of fluorescence observed at the time of imaging the fluorescent image described above (reference measurement position) is at least positioned within the view field. The transmission light image may be imaged by emitting a continuous spectrum in the visible light range to detect the transmission light 9 through the biological sample 1 by the two dimensional color image sensor 11. The transmission light image detected by the two dimensional color image sensor 11 is stored in the transmission light image storage unit 13 as the image data having 8 bits each for R, G, B colors.

At this point, imaging the transmission light image may be sufficient to perform on the area adjacent to the observed fluorescence. This allows the transmission light image to be imaged at a higher resolution. For example, when using a CCD of the size 12 mm square, 1000 by 1000 pixels for the two dimensional color image sensor 11, and the magnification power of 30 by the transmission light optics 10, a pixel of the size of 0.4 μm minimum can obtain a transmission light image for the field of 0.4 mm square. However, the optical resolution determined by the transmission light optics 10 should be equal to or less than 0.4 μm in this case. In contrast to this, when imaging the fluorescent image described above, the entire surface area of the sample 1 is required to be examined. Accordingly, in condition that the area to be examined on the sample 1 is 20 by 40 mm, the number of pixels of the fluorescent image is 2000 by 4000, then the resolution or the size of a pixel is 10 μm.

With respect to the resolution of a transmission light image, 0.1 to 1 μm is preferable, since the size of typical cells is approximately 10 μm, and the size of typical nuclei is approximately 2 μm, because the transmission light image needs to resolve at least the nuclei. With respect to the resolution of a fluorescent image, the resolution may need not to be comparable to the transmission light image since the examination needs only to determine whether the fluorescence from the fluorescent label bound to the probe DNA is emitted intranuclear or extranuclear, or whether the fluorescence comes from location intracellular or extracellular. More specifically, it is preferable for the resolution of transmission light images to set to 2 to 20 times of the resolution of fluorescent images.

Thereafter, the fluorescent image stored in the fluorescent image storage unit 12 is superimposed on the corresponding transmission light image stored in the transmission light image storage unit 13 to display on the image display unit 16. At this time the fluorescent image is read out from the fluorescent image storage unit 12 to store in the image buffer 14, then the transmission light image is read out from the transmission light image storage unit 12 to store in the image buffer 14. Then the fluorescent image and transmission light image both stored in the image buffer 14 are processed by the image data processor unit 15 to composite the screen display data.

The term "corresponding" indicates that the mutual position of the fluorescent image and transmission light image are virtually adjusted or controlled based on the positional information from the sample or the biological sample holder unit 2 carrying the sample.

Figure 4:
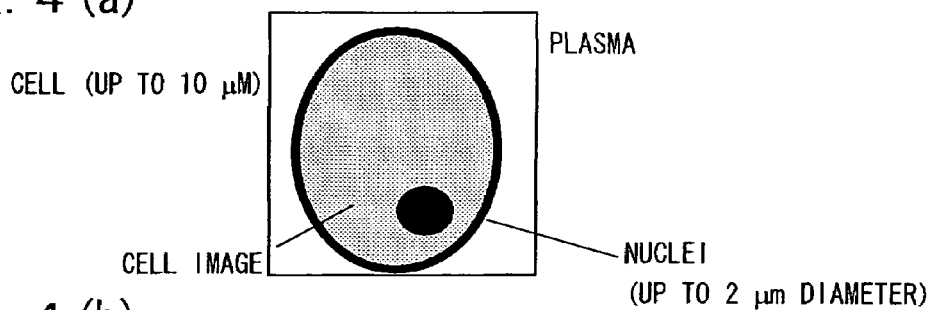
FIG. 4a is a schematic diagram illustrating the merge a fluorescent image and a transmission light image, indicating a cell to be measured.
FIG. 4b is a schematic diagram illustrating the merge a fluorescent image and a transmission light image, indicating a fluorescent image.
FIG. 4c is a schematic diagram illustrating the merge a fluorescent image and a transmission light image, indicating a transmission light image.
FIG. 4d is a schematic diagram illustrating the merge a fluorescent image and a transmission light image, indicating an exemplary merged image.
FIG. 4e is a schematic diagram illustrating the merge a fluorescent image and a transmission light image, indicating another exemplary merged image.
FIG. 4f is a schematic diagram illustrating the merge a fluorescent image and a transmission light image, indicating still another exemplary merged image.
Figure 4:
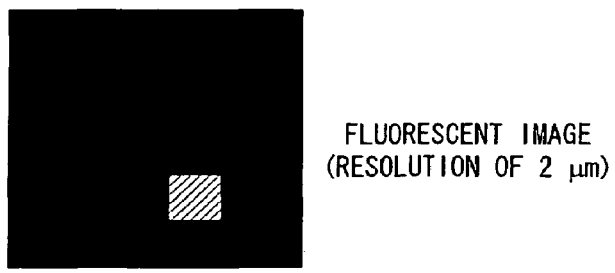
Figure 4:
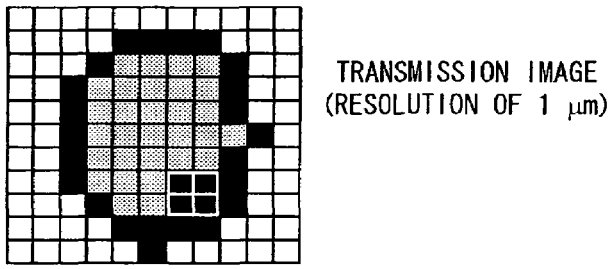
Figure 4:
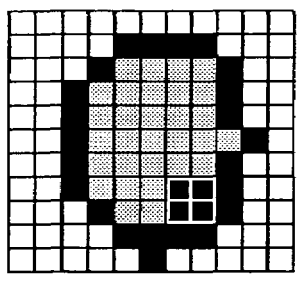
Figure 4:
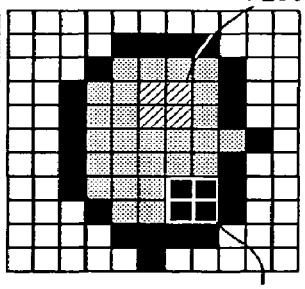
Figure 4:
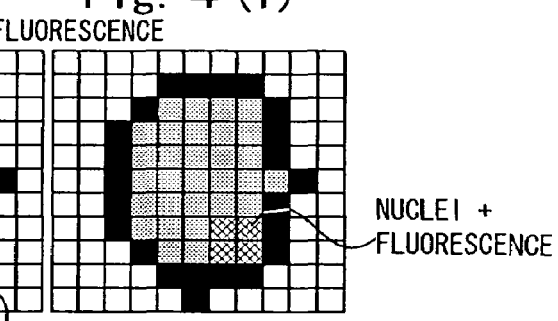

For example, when imaging a fluorescent image of the cell shown in FIG. 4a with the size of pixels of 2 μm as shown in FIG. 4b, and imaging a transmission light image with the size of pixels of 1 μm as shown in FIG. 4c, the resolution of fluorescent image is twice the transmission light image, so that one pixel of image data in the fluorescent image storage unit 12 is read out after splitting to 2 by 2=4 subpixels.

The number of split of a pixel depend on the ratio of resolution of the fluorescent image to the transmission light image, and in case of the above example that the resolution of fluorescent image is 10 μm and the resolution of transmission light image is 0.5 μm, one pixel of fluorescent image is split into 20 by 20=400 subpixels. Also the image buffer 14 is conformed to the pixels of fluorescent images, 8 bits per pixel for respective R, G, B colors. The image data of fluorescent image of 16 bits monochrome is upconverted in the image data processor unit 15 to be mapped to 24 bits gray-scale data. The screen display data may be obtained at the image data processor unit 15 by logic-ORing pixel data of 24 bits of the fluorescent image and that of corresponding transmission light image in the image buffer 14. Thus obtained screen display data is stored in the image buffer 14. By displaying on the image display unit 16 the screen display data stored in the image buffer 14, the composite screen display of a fluorescent image and a transmission light image can be observed on-screen.

As possible results of superimposing a fluorescent image and a transmission light image, screen display data may be displayed on the image display unit 16 as shown in FIGS. 4d, 4e, and 4f. FIG. 4d indicates a case in which no fluorescence from the fluorescent label is detected, implying the absence of the DNA derived from the virus to be examined. FIG. 4e indicates a case in which the fluorescence from the fluorescent label is detected in the cytoplasm, implying the presence of the DNA derived from the virus to be detected in the cytoplasm. FIG. 4f indicates a case in which the fluorescence of the fluorescent label is detected in the nuclei, implying the presence of the viral DNA subject to be examined in the nuclei.

In accordance with the preferred embodiment, for examining positive/negative diagnosis by detecting the fluorescent from fluorescent label, by displaying a merged image of a transmission light image and a fluorescent image rich information can be obtained therefrom. More specifically, the information can be used not only for determination of positive/negative result based on the detection of fluorescence but also for more specific determination of location of fluorescence. In particular, the optical measurement apparatus images the transmission light image at a higher resolution than the fluorescent image. In such a case the location of emitted fluorescence can be identified with utmost preciseness.

Also in this embodiment the fluorescent image is captured prior to imaging the transmission light image, for a transmission light image to be imaged so as to include at least the location of detected fluorescence. In other words, an entire cell to be examined may not need to be imaged to the transmission light image, it is sufficient to image only a part in doubt of that cell. Consequently the amount of data to be recorded in the transmission light image storage unit can be saved if the transmission light image resolution is enough high.

In addition, the preferred embodiment detects the fluorescence from the fluorescent label by emitting the exciting laser to the sample 1. This allows the radiation density with respect to the sample 1 to be increased to detect the fluorescence of the fluorescent label at a higher sensitivity. Accordingly this allows increasing the detection probability of the cell containing the DNA derived from the subject virus to be examined. Also the optical measurement apparatus described in the preferred embodiment uses the X axis direction fine adjuster stage 3-3 and the Y axis direction fine adjustment stage 3-4 at the time of scanning the exciting laser beam, and uses the X axis direction coarse adjustment stage 3-5 at the time of switching over from the fluorescent image imaging to the transmission light image imaging. In accordance with this optical measurement apparatus, an accurate registration and a transition may be achieved at a shorter time as well as at a higher precision.

Figure 5:
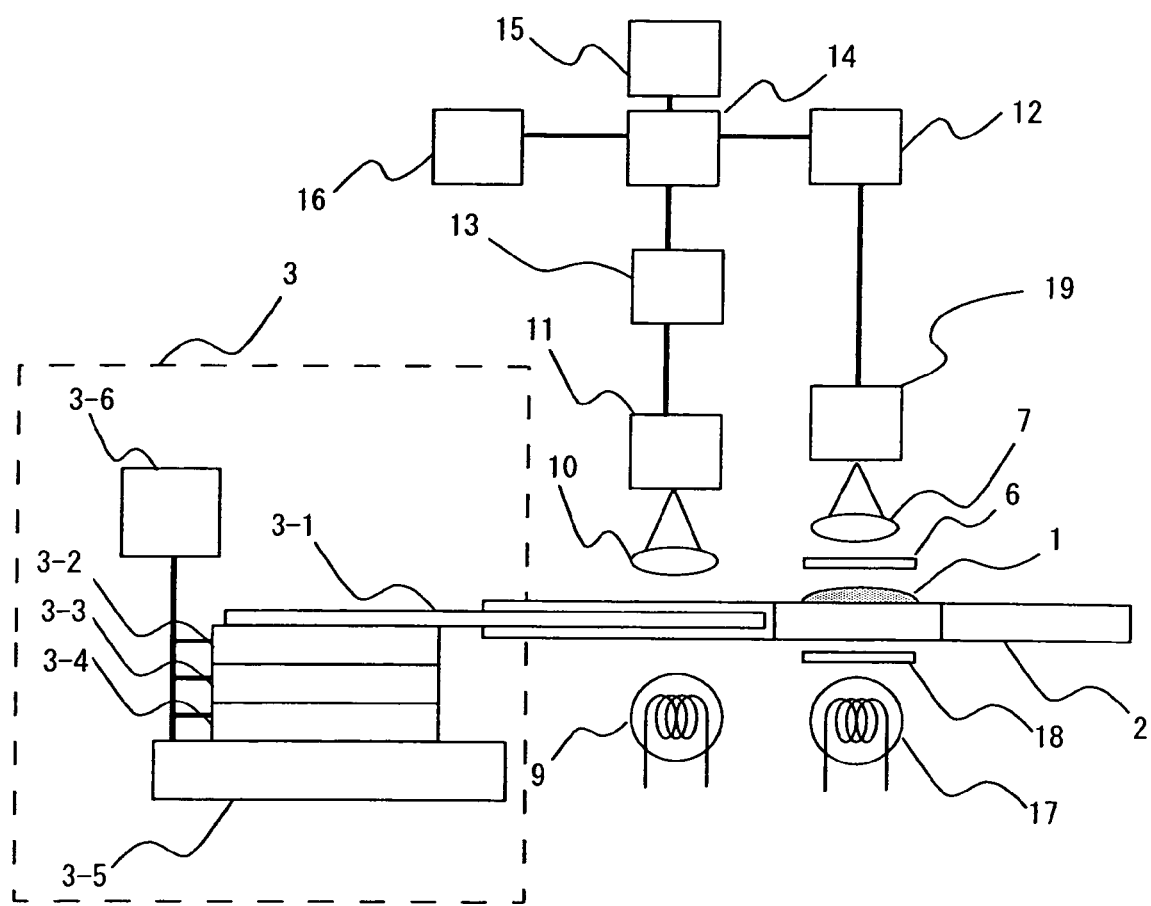
FIG. 5 is a schematic diagram of substantial part of another biological sample optical measurement apparatus incorporating the present invention.

It can be appreciated by those skilled in the art that the present invention is not limited to the optical measurement apparatus as have been described above, and that the present invention may equally be embodied as an optical measurement apparatus shown in FIG. 5. The optical measurement apparatus shown in FIG. 5 comprises a mercury-vapor lamp 17 for exiting diffused light for exciting the fluorescent label, a bandpass filter 18 for removing the light of wavelength equal to the wavelength of fluorescence of the fluorescent label from within the wavelengths contained in the diffused light, and a two dimensional monochrome image sensor 19 such as a CCD for detecting the fluorescence from the fluorescent label excited in the sample 1. In this optical measurement apparatus embodiment, an Mercury-vapor lamp 17 is used for emitting diffused light, however the present invention is not limited thereto and any other type of appropriate diffused light source, which is capable of emitting diffused light, may equally be used instead, including a Xe (xenon) lamp, Hg—Xe (mercury-xenon) lamp and the like. For the bandpass filter 18 a filter that eliminates any wavelength components other than 600 to 650 nm band, when using Cy-5(R) as have been described above for example. The optical measurement apparatus described in this embodiment has the identical configuration as the preceding embodiment of optical measurement apparatus shown in FIG. 1.

The optical measurement apparatus configured as described above may emit diffused light to the sample 1 through the bandpass filter 18 when imaging a fluorescent image. Then the apparatus may detect fluorescence from a predetermined zone in the biological sample holder unit 2 by means of the two dimensional monochrome image sensor 19.

The fluorescent image detected by the two dimensional monochrome image sensor 19 is stored in the fluorescent image storage unit 12.

The optical measurement apparatus of the present embodiment emits diffused light to the sample 1 to detect fluorescence by the two dimensional monochrome image sensor 19, without the need of scanning the diffused light by driving the biological sample holder driving unit 3, as has been required in the optical measurement apparatus shown in FIG. 1. The optical measurement apparatus shown in FIG. 5 may detect thereby the fluorescence from the sample 1 in a considerable shorter period of time.

In particular, the present optical measurement apparatus may not need to replace the Mercury-vapor lamp 17 as the diffused light source, for any fluorescent labels, but sufficient to replace the bandpass filter 18 according to the wavelength of excitation light to excite the fluorescent label used. More specifically, the optical measurement apparatus of the present embodiment allows transmit any desired wavelength included in the diffused light emitted from the Mercury-vapor lamp 17 by replacing solely the bandpass filter 18, in order to excite any fluorescent label.

In accordance with the present optical measurement apparatus, when examining the fluorescence from a sample 1 by using a plurality of fluorescent labels each having a different excitation wavelength, the fluorescence of a plurality of fluorescent labels can be sequentially detected by using a plurality of band-pass filters 18, each corresponding to one of excitation wavelengths one after another.

For a plurality of types of virus, for example HPV, the strain is classified into three groups of high-, low-, and intermediate-risk. A hybridization using a probe DNA having different fluorescent label bound thereto which is accommodating to these three types of virus species for a sample 1 may be achievable. In such a circumstance the fluorescent images by each of a plurality of wavelengths from the sample 1 can be examined, one at a time, by providing a plurality of bandpass filters 18 each corresponding to respective three fluorescent labels, and by switching appropriately the plurality of band-pass filters 18 during the measurement. In this manner, the strain of infection to the sample 1 can be identified by the optical measurement apparatus, and the infected site of three strains can be determined.

When measuring fluorescent image by the present embodiment of optical measurement apparatus, assuming using the size of examination area R of 20 by 40 mm, and the number of pixels of the two dimensional monochrome image sensor 19 of 1000 by 1000 pixels, and using the magnification power of 1/10 of reductive optics for the fluorescence optics 7, a fluorescent image of pixel size of 10 μm can be imaged by examining the image of the examination area R by two paths while moving the field by the X axis direction fine adjuster stage 3-3.

After having imaged the fluorescent image, in a manner similar to the optical measurement apparatus shown in FIG. 1, the imaging of transmission light image, merge fluorescent image and transmission light image, and display of merged image may be performed. In accordance with the present embodiment, the fluorescence excitation by the Mercury-vapor lamp 17 of diffuse light source and the fluorescence detection by the two dimensional monochrome image sensor 19 allows imaging of the fluorescent image of a wider area on the sample 1 at a shorter time, resulting in an increased throughput of primary screening examination if there is a number of samples.

Although examples have been shown as optical measurement apparatus shown in FIG. 1 and FIG. 5, by binding a fluorescent label to the probe DNA to image the fluorescent image of the sample 1, chemical or biological luminescent label substance can be bound to the probe DNA. In such cases, the luminescent reaction of chemical or biological luminescent substance is carried out in a solution. To do this a reagent dripper unit for dripping drops of the reagent to the sample 1 is preferably provided to the optical measurement apparatus.

Also in such cases, it is preferable to use a cover glass or the like to flatten the surface of dripped solution on the sample 1 during the luminescence measurement to prevent the shift of focal plane. However, the flattening of solution surface by means of a cover glass is not necessary if the luminescent image detecting system is configured such that the measurement of luminescence is carried out from the downside of the biological sample holder unit 2. In this situation the biological sample holder unit 2 is required to be transparent to the luminescence of the chemical or biological luminescence substance. When using a chemical or biological luminescence substance for the label instead of fluorescent label, the laser light source 4 for excitation of the fluorescent label, the excitation light optics 5, the long-pass filter 6, the bandpass filter 18 and the like may not need to be provided. Therefore when using a chemical or biological luminescence substance for the label, the optics in the optical measurement apparatus can be simplified, allowing downsizing the apparatus, as well as decreasing the cost.

Figure 6:
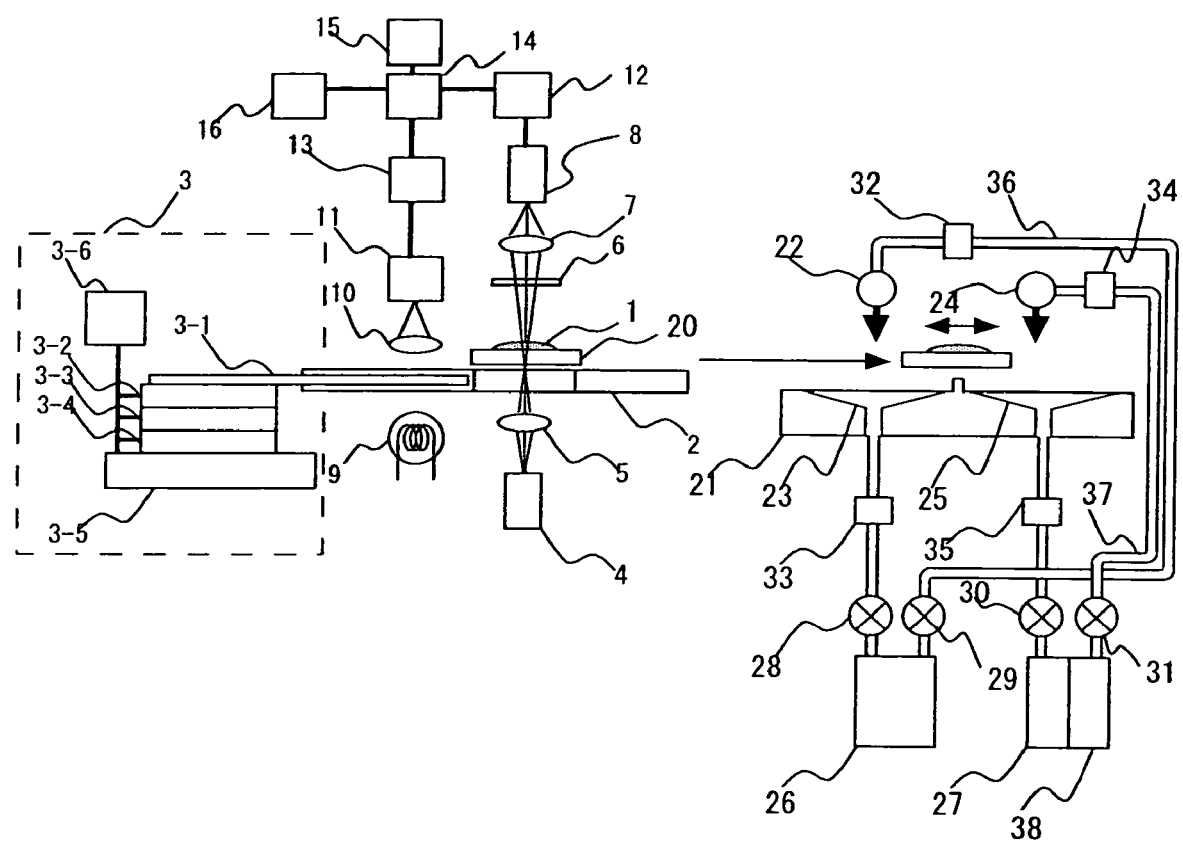
FIG. 6 is a schematic diagram of substantial part of still another biological sample optical measurement apparatus incorporating the present invention.
Figure 7:
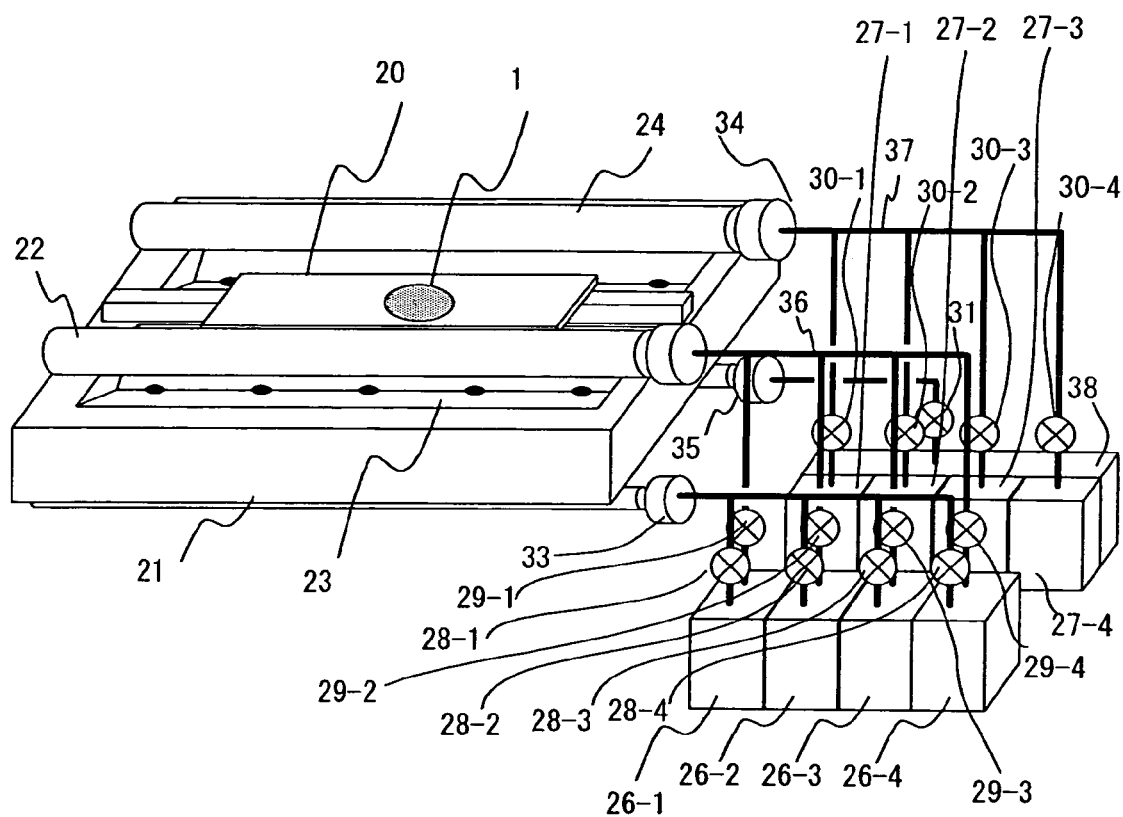
FIG. 7 is a perspective view of substantial part of sample staining unit of the biological sample optical measurement apparatus shown in FIG. 6.

The optical measurement apparatus applied to the present invention may have, as shown in FIG. 6 and FIG. 7, a reagent staining unit 21 for staining the sample 1 prior to imaging the transmission light image. In this embodiment, the sample 1 is mounted on a biological sample holder unit 20 with identification marks. In the optical measurement apparatus shown in FIG. 6 and FIG. 7, a sample staining unit 21 comprises a staining section consisting a staining solution sprayer unit 22 and solution collecting unit 23, and rinse section consisting a rinse solution sprayer unit 24 and rinse collecting unit 25. The optical measurement apparatus may also comprise a motion controller means for moving the biological sample holder unit 20 with identification mark into the direction shown by the arrow A in FIG. 6.

The staining solution sprayer unit 22 is formed of a cylinder member with a plurality of spray nozzles pierced at the side opposing to the solution collecting unit 23. The plurality of spray nozzles may be provided to spray the staining solution and the like to at least the entire sample 1 at the time when the biological sample holder unit 20 with identification mark is moved by the motion controller means. The rinse solution sprayer unit 24 is formed of a cylinder member having a plurality of spray nozzles pierced at the side opposing to the rinse collecting unit 25. The solution collecting unit 23 and the rinse collecting unit 25 comprise waste outlet formed at the bottom of the units, and a inclined ramp down to the waste outlet, respectively. Between the solution collecting unit 23 and the rinse collecting unit 25 there is formed a projected rail for preventing the mixture of stain and rinse.

The staining solution sprayer unit 22 is connected to a group of stain solution containers 26 through stain solution tubings 36. One end of the stain solution tubings 36 is connected to the staining solution sprayer unit 22, the other end to the waste outlet of the solution collecting unit 23. The stain solution tubings 36 between the staining solution sprayer unit 22 and the stain solution containers 26 have a stain solution feeder pump 32 and an electromagnetic valve 29. The stain solution tubings 36 between the solution collecting unit 23 and the stain solution containers 26 may have a stain solution feeder pump 33 and electromagnetic valves 28 (28-1, 28-2, 28-3, 28-4).

Similarly, the rinse solution sprayer unit 24 is connected to a group of rinse solution containers 27 through rinse solution tubings 37. The waste outlet of the rinse collecting unit 25 is connected to a waste rinse solution container 38 through a rinse solution tubings 37. The rinse solution tubings 37 between the rinse solution sprayer unit 24 and the rinse solution containers 27 may have a rinse solution feeder pump 34 and an electromagnetic valve 31. The rinse solution tubings 37 between the rinse collecting unit 25 and the waste rinse solution container 38 may have a rinse solution feeder pump 35 and electromagnetic valves 30 (30-1, 30-2, 30-3, 30-4).

The stain solution containers 26 may comprise, for example as shown in FIG. 7, a stain A container 26-1, a stain B container 26-2, a clearing solution container 26-3, a tubing cleaning solution container 26-4. In other words, the stain solution containers 26 comprises a plurality of containers each stores separately a reagent required for staining for imaging the transmission light image of the sample 1, and the rinse solution for washing the stain solution tubings 36. The communication from the stain A container 26-1, the stain B container 26-2, the clearing solution container 26-3, the tubing cleaning solution container 26-4 to the stain solution tubings 36 is controlled by the electromagnetic valves 28-1, 28-2, 28-3, 28-4 provided in the middle of the stain solution tubings 36, respectively.

The rinse solution containers 27 comprise, as shown in FIG. 7, a rinse solution container 27-1, a fractioning solution container 27-2, an affinity solution A container 27-3, and an affinity solution B container 27-4. In other words, the rinse solution containers 27 comprise a plurality of containers each storing separately a reagent necessary for rinsing, fractioning, and affinity treatment after staining. The communication of rinse solution container 27-1, the fractioning solution container 27-2, the affinity solution A container 27-3, and the affinity solution B container 27-4 with the rinse solution tubings 37 is controlled by the electromagnetic valves 30-1, 30-2, 30-3, and 30-4 provided in the middle of the rinse solution tubings 37, respectively. The communication with the waste rinse solution container 38 is controlled by the electromagnetic valve 31.

The optical measurement apparatus configured as have been described above, after having imaged a fluorescent image in a manner similar to the preceding embodiment, and prior to imaging the transmission light image, may stain the sample 1. In the following, as an example of staining, HE (Haematoxylin-Eosin) staining is used for the sake of description. In haematoxylin eosin staining, haematoxylin stains mostly the nuclei in the cell to blue-purple, while eosin stains the plasma, intercellular substance, and fibrin to burned umber or dark brown. In accordance with this staining method generic intracellular information can be obtained as a transmission light image in just proportion. This staining method therefore is one of staining methods commonly used in the field of pathologic diagnosis. With this staining a highly accurate transmission light image can be obtained, allowing a highly accurate diagnosis on the presence or absence of infection, or the identification of infected lesion in the viral infection diagnosis.

In staining procedure, the biological sample holder unit 2 is moved in the direction shown by an arrow A in the FIG. 6 by means of a motion controller means not shown in the figure to carry the biological sample holder unit 2 into the sample staining unit 21.

Next, haematoxylin stain solution supplied from the stain A container 26-1 is sprayed onto the biological sample 1 through the staining solution sprayer unit 22 for four (4) minutes. When spraying haematoxylin solution, the valves 28-1 and 29-1 are opened while operating the stain solution feeder pump 32 and the stain solution collecting pump 33. In this manner only haematoxylin solution is supplied to spray without being mixed with other staining solutions contained in other containers than the stain A container 26-1, and thus sprayed haematoxylin solution can be collected to the solution collecting unit 23. Collected haematoxylin solution is pumped up to the stain A container 26-1 to reuse.

Next, the biological sample holder unit 2 is moved to the rinse section by the motion controller means not shown in the figure to rinse the sample 1 with distilled water supplied from the rinse solution container 26-1 through the rinse solution sprayer unit 24 for about five minutes to wash out stain. For feeding distilled water only the valves 30-1 and 31 are opened to operate the rinse solution feeder pump 34 and the rinse solution collection pump 35. In this manner only distilled water is supplied to spray without being mixed with other solutions contained in other containers than the rinse solution container 26-1, and thus supplied distilled water can be collected to the waste rinse solution container 38 through the rinse collecting unit 25.

During rinse described above, the valves 28-1 and 29-1 are closed while the valves 28-4 and 29-4 are opened to operate the rinse solution feeder pump 34 and the rinse solution collection pump 35. In this manner distilled water from the tubing cleaning solution container 26-4 may be supplied to the staining solution sprayer unit 22 and to stain solution tubings 36 for washing out haematoxylin solution residue in the staining solution sprayer unit 22 and the stain solution tubings 36. The distilled water supplied to the staining solution sprayer unit 22 and to stain solution tubings 36 are collected through the solution collecting unit 23.

Then, a mixture of 0.2% hydrochloric acid and 70% alcohol supplied from the fractioning solution container 27-2 is supplied to the sample 1 through the rinse solution sprayer unit 24. For fractioning, the valves 28-2 and 29-2 are opened to operate the rinse solution feeder pump 34 and the rinse solution collection pump 35. After fractioning, another rinse by distilled water is carried out at the rinse section in a manner identical to that described above.

Next, an affinity treatment is carried out by spraying 95% alcohol solution supplied from the affinity solution A container 27-3 to the biological sample 1. During affinity treatment, the valves 28-3 and 29-3 are opened to operate the rinse solution feeder pump 34 and the rinse solution collection pump 35. The fractioning is the last step of haematoxylin staining.

After haematoxylin staining, another stain by eosin solution is carried out. In the eosin staining, the biological sample holder unit 2 is moved to the staining section by means of the motion controller unit not shown in the figure, to spray eosin-phloxin B mixture supplied from the stain B container 26-2 for seven minutes for staining. When spraying eosin-phloxin B mixture the valves 28-2 and 29-2 are opened to operate the stain solution feeder pump 32 and the stain solution collecting pump 33. In this manner only eosin-phloxin B mixture is sprayed without being mixed with any other solutions contained in other containers than the stain B container 26-2, and thus sprayed eosin-phloxin B mixture can be collected through the solution collecting unit 23. Collected eosin-phloxin B mixture is pumped up to the stain B container 26-2 to reuse.

Next, the biological sample holder unit 2 is moved to the rinse section by the by the motion controller means not shown in the figure to rinse the sample 1 with distilled water in a manner similar to haematoxylin stain process, to wash out eosin-phloxin B residue in the staining solution sprayer unit 22 and the stain solution tubings 36.

Thereafter, 95% alcohol solution is sprayed to the biological sample 1, and then the absolute alcohol supplied from the affinity solution B container 27-4 is sprayed thereto to fractionation and dehydration. During this fractionation and dehydration, the valves 28-4 and 29-4 are opened to operate the rinse solution feeder pump 34 and the rinse solution collection pump 35.

Then, the biological sample holder unit 2 is moved to the stain section by the motion controller means not shown in the figure to lucidify by spraying xylol supplied from the clearing solution container 26-3 to the biological sample 1. During lucidification only the valves 28-3 and 29-3 are opened to operate the stain solution feeder pump 32 and the stain solution collecting pump 33. After lucidification xylol in the staining solution sprayer unit 22 and the stain solution tubings 36 are removed in a manner similar to the rinse process described above.

All staining steps for the biological sample 1 are complete at this point. After staining, the biological sample holder unit 20 with identification mark is carried to the opposite direction of the arrow A in FIG. 6 and fixedly held to image the transmission light image of the biological sample 1. The imaging of the transmission light image is carried out as similar to the foregoing embodiment. In accordance with this embodiment, since the optical measurement apparatus is capable to staining the sample, the measurement of the transmission light image after staining process after the imaging of the fluorescent image can be performed in a shorter time. In accordance with the optical measurement apparatus of the present embodiment, a number of samples 1 may be processed in a short period of time, for example for viral inspection, contributing to the effective improvement of the throughput. The optical measurement apparatus in accordance with the preferred embodiment reuses the staining solution by recycling to suppress the total quantity consumed of the staining solution during the inspection of a number of samples 1.

The haematoxylin staining solution used in the above embodiment has the ingredient as follows:
Haematoxylin: 5 g
Distilled Water: 700 ml.
Ammonium alum: 50 g
Sodium iodate: 0.5 g
Glycerin: 300 ml.

The eosin-phloxin B mixture solution used in the above embodiment has the ingredient as follows:
1% eosin 100 ml.
Eosin Y: 1 g
Distilled Water: 100 ml.
1% phloxin B: 10 ml.
Phloxin B: 1 g
Distilled Water: 100 ml.
95% alcohol: 780 ml.
Glacial acetic acid: 5 ml.

The publications, patents, and patent applications cited in this specification are incorporated in this document.

INDUSTRIAL APPLICABILITY OF THE INVENTION

As have been described above in details, a method of optical measurement of biological samples and an apparatus of optical measurement of biological samples may superimposingly display a fluorescence or luminescence image and a corresponding transmission light image derived from a sample to facilitate detection of accurate location of fluorescence or luminance in a given area on the sample.

The invention claimed is:

1. A method of optical measurement of biological samples, comprising the steps of:
imaging fluorescent or luminescence image of at least a part of a biological sample;
imaging a transmission light image of at least a part of said biological sample; and
displaying said fluorescent or luminescence image and said transmission light image superimposingly, such that said fluorescent or luminescence image of said biological sample correspond to said transmission light image of said biological sample;
wherein:
said transmission light image has much higher resolution in comparison with said fluorescent or luminescence image.

2. A method of optical measurement of biological samples of claim 1, wherein:
the resolution of said transmission light image is in the range of from twice to twenty times of the resolution of said fluorescent or luminescence image.

3. A method of optical measurement of biological samples of claim 1, wherein:
after having captured said fluorescent or luminescence image said biological sample is stained and then said transmission light image is imaged.

4. A method of optical measurement of biological samples of claim 1, wherein:
with reference to an optical identification mark, provided on a retainer for retaining said biological sample for registration, said fluorescent or luminescence image and said transmission light image are registered for imaging.

5. An apparatus of optical measurement of biological samples, which comprises:
image data storage capability for storing fluorescent or luminescence image having at least a part of a biological sample measured and transmission light image having at least a part of said biological sample measured; and
computing capability for computing on said fluorescent or luminescence image and said transmission light image;
wherein:
said fluorescent or luminescence image and said transmission light image stored in said image data storage capability are processed by said computing capability to then display said fluorescent or luminescence image and said transmission light image superimposingly,
and said optical measurement means images said fluorescent or luminescence image at a higher resolution than said transmission light image.

6. An apparatus of optical measurement of biological samples of claim 5, which further comprises:
an optical measurement means for measuring said fluorescent or luminescence image and said transmission light image.

7. An apparatus of optical measurement of biological samples of claim 5, which further comprises:
a holder for holding said biological sample having optical identification marks;
wherein:
said fluorescent or luminescence image is imaged registered with said transmission light image.

8. An apparatus of optical measurement of biological samples set forth in claim 7, in which:
said optical identification mark is a plurality of circle patterns; and the registration for imaging of said fluorescent or luminescence images and transmission light image is performed by referencing a center point coordinate of said circle pattern obtained from the image data of said optical identification mark.

9. An apparatus of optical measurement of biological samples of claim 6 wherein:

said optical measurement means images said fluorescent or luminescence images, then the transmission light image after having stained said biological sample for transmission light image measurement.

10. An apparatus of optical measurement of biological samples of claim 5 which further comprises:

a staining means for staining said biological sample.

11. An apparatus of optical measurement of biological samples of claim 5 wherein:

a fluorescent or luminescence image is obtained from the biological sample having fluorescent or luminescence substance conjugated, thereafter a transmission light image is obtained from said biological sample having stained.

12. An apparatus of optical measurement of biological samples, which comprises:

a fluorescence or luminescence detecting unit for detecting fluorescence or luminescence emerged from a biological sample;

a transmission detecting unit for emitting light to said biological sample and for detecting the transmission light of the emitted light having passed through said biological sample;

an image storage unit for storing image data of fluorescent or luminescence images measured by said fluorescence or luminescence detecting unit and transmission light images measured by said transmission detecting unit;

image data processing unit for processing image data of said fluorescent or luminescence images and image data of said transmission light images stored on said image data storage unit; and image display unit for displaying said fluorescent or luminescence image superposed on said transmission light image after having processed on said image data processing unit said image data of said fluorescent or luminescence image and said image data of said transmission light image;

wherein:

said fluorescence or luminescence detecting unit has fluorescence excited from said biological sample input for two dimensional image information, said transmission detector unit has transmission light image information of higher resolution than the two dimensional image information input to said fluorescence or luminescence detector unit.

13. An apparatus of optical measurement of biological samples of claim 12, wherein:

said fluorescence or luminescence detecting unit emits an optical beam to scan said biological sample in order to detect fluorescence excited by the emitted optical beam from said biological sample.

14. An apparatus of optical measurement of biological samples of claim 12, wherein:

said fluorescence or luminescence detecting unit detects light luminescence caused by the luminescence treatment processed to said biological sample.

\* \* \* \* \*